United States Patent
Jackson et al.

(10) Patent No.: US 10,627,229 B2
(45) Date of Patent: *Apr. 21, 2020

(54) ELECTRONIC DEVICES WITH PRESSURE SENSORS FOR CHARACTERIZING MOTION

(71) Applicant: Apple Inc., Cupertino, CA (US)

(72) Inventors: Stephen P. Jackson, San Francisco, CA (US); Hung A. Pham, Oakland, CA (US); Anh N. Phan, Milpitas, CA (US); Shameek P. Ganguly, Sunnyvale, CA (US)

(73) Assignee: Apple Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/148,444

(22) Filed: Oct. 1, 2018

(65) Prior Publication Data

US 2019/0101387 A1 Apr. 4, 2019

Related U.S. Application Data

(63) Continuation of application No. 14/848,690, filed on Sep. 9, 2015, now Pat. No. 10,088,308.

(60) Provisional application No. 62/048,177, filed on Sep. 9, 2014.

(51) Int. Cl.
| | |
|---|---|
| *G06F 11/30* | (2006.01) |
| *G01C 5/00* | (2006.01) |
| *G01C 22/00* | (2006.01) |
| *A61B 5/11* | (2006.01) |
| *G01P 15/00* | (2006.01) |

(52) U.S. Cl.
CPC .............. *G01C 5/00* (2013.01); *A61B 5/1123* (2013.01); *G01C 22/006* (2013.01); *A61B 2560/0257* (2013.01); *G01P 15/00* (2013.01)

(58) Field of Classification Search
CPC ....................................................... G01C 5/00
See application file for complete search history.

(56) References Cited

U.S. PATENT DOCUMENTS

| 8,180,591 | B2* | 5/2012 | Yuen | A61B 5/0002 |
| | | | | 702/160 |
| 10,088,308 | B2* | 10/2018 | Jackson | G01O 5/00 |
| 2014/0031703 | A1 | 1/2014 | Rayner et al. | |
| 2014/0125480 | A1 | 5/2014 | Utter, II | |

(Continued)

*Primary Examiner* — Phuong Huynh
(74) *Attorney, Agent, or Firm* — Treyz Law Group, P.C.; Kendall W. Abbasi

(57) ABSTRACT

An electronic device may include a motion sensor for detecting movement of the electronic device and a pressure sensor for detecting changes in elevation of the electronic device. Applications that run on the electronic device such as health and fitness applications may use motion sensor and pressure sensor data to track a user's physical activity. For example, processing circuitry in the electronic device may use the motion sensor to track a user's steps and the pressure sensor to track changes in the user's elevation. The processing circuitry may determine whether the user is climbing stairs based on the user's step rate and the user's changes in elevation. When the processing circuitry determines that the user is climbing stairs, the processing circuitry may use the pressure sensor and motion sensor to track and store the number of flights of stairs climbed by the user.

20 Claims, 9 Drawing Sheets

(56) References Cited

U.S. PATENT DOCUMENTS

2014/0278139 A1* 9/2014 Hong ............... A61B 5/4866
                                                    702/19
2015/0221232 A1   8/2015 Ziv et al.

* cited by examiner

ELECTRONIC DEVICES WITH PRESSURE SENSORS FOR CHARACTERIZING MOTION This application is a continuation of patent application Ser. No. 14/848,690, filed Sep. 9, 2015, which claims the benefit of provisional patent application No. 62/048,177, filed Sep. 9, 2014, both of which are hereby incorporated by reference herein in their entireties.

BACKGROUND

This relates generally to electronic devices and, more particularly, to electronic devices with sensor circuitry for detecting and characterizing a user's movement.

Electronic devices are sometimes provided with motion sensors such as accelerometers that are configured to detect a user's movement. Applications that run on an electronic device may use motion sensor information to track a user's physical activity. For example, a fitness application running on an electronic device may use motion sensor data to log or record how long or far a user runs or walks.

Conventional electronic devices determine what type of physical activity is being performed (e.g., walking, running, etc.) based solely on the output from an accelerometer. Relying exclusively on accelerometer signals to determine what type of activity is being performed by a user can lead to inaccuracies. For example, accelerometer signals that are collected while a user is walking may sometimes look similar to accelerometer signals that are collected while a user is cycling. As another example, accelerometer signals that are collected while a user is climbing a set of stairs may sometimes look similar to accelerometer signals that are collected while a user is cycling.

It would therefore be desirable to be able to provide improved ways of using an electronic device to characterize the movement of a user.

SUMMARY

An electronic device may include a motion sensor such as one or more accelerometers, gyroscopes, and/or compasses for detecting movement of the electronic device. Applications that run on the electronic device such as fitness applications or activity logging applications may use motion sensor data to track a user's physical activity.

To avoid mischaracterizing a user's movement, processing circuitry in an electronic device may supplement motion sensor data with additional information in instances where motion sensor data alone is insufficient to distinguish between different types of physical activity.

For example, information on a user's elevation may be synthesized with motion sensor data to help characterize a user's movement. Information on a user's elevation may be determined using one or more pressure sensors (e.g., one or more barometers). Air pressure information gathered using a pressure sensor may be used to determine a user's altitude and/or a user's change in altitude over a given amount of time. This information may in turn be used in combination with motion sensor data to characterize and track a user's movement.

For example, processing circuitry in the electronic device may use a motion sensor to track a user's steps and a pressure sensor to track changes in the user's elevation. The processing circuitry may determine whether the user is climbing stairs based on the user's step rate and the user's changes in elevation.

To determine if the user is climbing stairs, the processing circuitry may use the pressure sensor data to determine the user's climb rate (e.g., the user's change in elevation over a given period of time) and may compare the climb rate with a minimum climb rate. The processing may use the motion sensor data to determine the user's step rate (e.g., the number of steps taken during a given period of time or over a given distance) and may compare the step rate with a minimum step rate and/or with a maximum step rate. If the user's climb rate exceeds the minimum climb rate and the user's step rate is within the upper and lower step rate limits, the processing circuitry may determine that the user is climbing stairs.

When the processing circuitry determines that the user is climbing stairs, the processing circuitry may use the pressure sensor and motion sensor data to track and store the number of flights of stairs climbed by the user.

DETAILED DESCRIPTION

Figure 1:
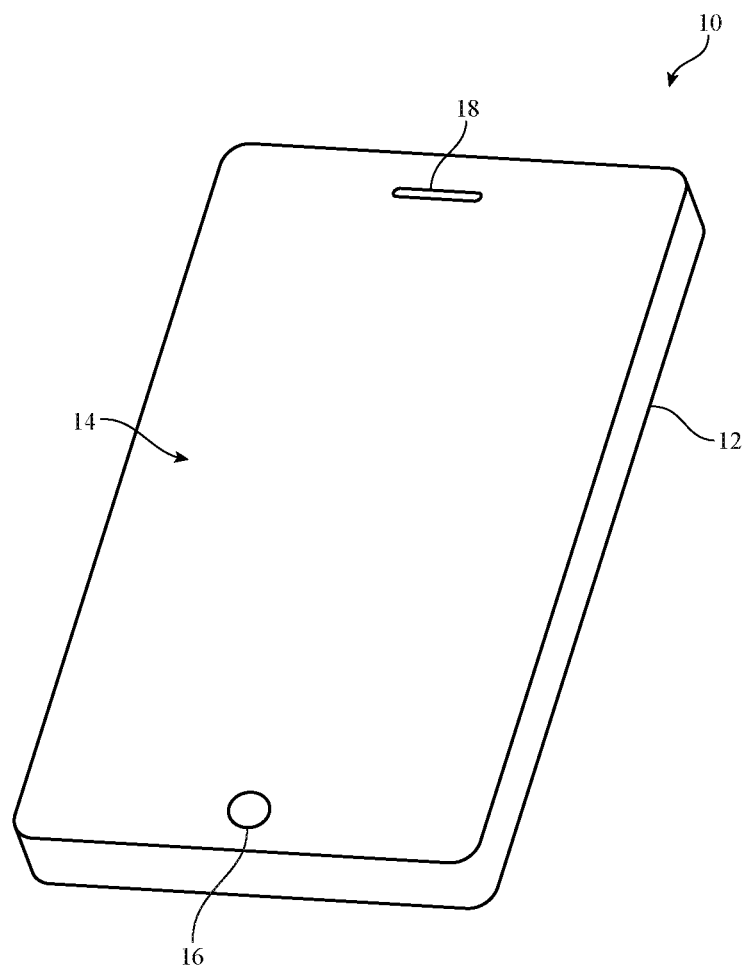
FIG. 1 is a perspective view of an illustrative electronic device of the type that may be provided with one or more pressure sensors in accordance with an embodiment of the present invention.

An illustrative electronic device that may be provided with motion characterization circuitry is shown in FIG. 1. Electronic device 10 of FIG. 1 may be a handheld electronic device or other electronic device. For example, electronic device 10 may be a cellular telephone, media player, or other handheld portable device, a somewhat smaller portable device such as a wrist-watch device, pendant device, or other wearable or miniature device, gaming equipment, a tablet computer, a notebook computer, a desktop computer, a television, a computer monitor, a computer integrated into a computer display, or other electronic equipment.

In the example of FIG. 1, device 10 includes a display such as display 14. Display 14 has been mounted in a housing such as housing 12. Housing 12, which may sometimes be referred to as an enclosure or case, may be formed of plastic, glass, ceramics, fiber composites, metal (e.g., stainless steel, aluminum, etc.), other suitable materials, or a combination of any two or more of these materials. Housing 12 may be formed using a unibody configuration in which some or all of housing 12 is machined or molded as a single structure or may be formed using multiple structures (e.g., an internal frame structure, one or more structures that form exterior housing surfaces, etc.).

Display 14 may be a touch screen display that incorporates a layer of conductive capacitive touch sensor electrodes or other touch sensor components (e.g., resistive touch sensor components, acoustic touch sensor components, force-based touch sensor components, light-based touch sensor components, etc.) or may be a display that is not touch-sensitive. Capacitive touch screen electrodes may be formed from an array of indium tin oxide pads or other transparent conductive structures.

Display 14 may include an array of display pixels formed from liquid crystal display (LCD) components, an array of electrophoretic display pixels, an array of plasma display pixels, an array of organic light-emitting diode display pixels, an array of electrowetting display pixels, or display pixels based on other display technologies. The brightness of display 14 may be adjustable. For example, display 14 may include a backlight unit formed from a light source such as a lamp or light-emitting diodes that can be used to increase or decrease display backlight levels and thereby adjust display brightness. Display 14 may also include organic light-emitting diode pixels or other pixels with adjustable intensities. In this type of display, display brightness can be adjusted by adjusting the intensities of drive signals used to control individual display pixels.

Display 14 may be protected using a display cover layer such as a layer of transparent glass or clear plastic. Openings may be formed in the display cover layer. For example, an opening may be formed in the display cover layer to accommodate a button such as button 16. An opening may also be formed in the display cover layer to accommodate ports such as speaker port 18.

In the center of display 14, display 14 may contain an array of active display pixels. This region is sometimes referred to as the active area of the display. A rectangular ring-shaped region surrounding the periphery of the active display region may not contain any active display pixels and may therefore sometimes be referred to as the inactive area of the display. The display cover layer or other display layers in display 14 may be provided with an opaque masking layer in the inactive region to hide internal components from view by a user.

Figure 2:
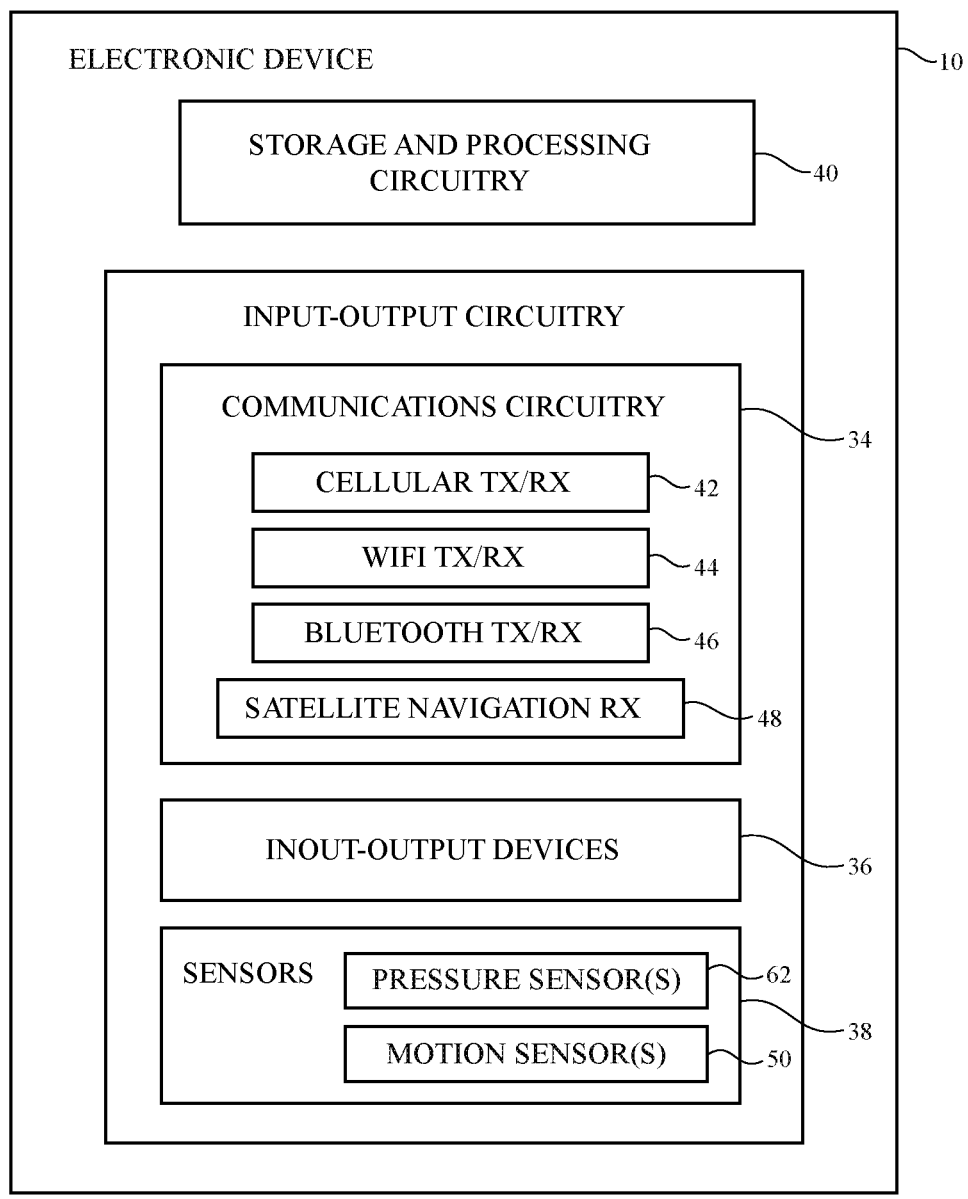
FIG. 2 is a schematic diagram of an illustrative electronic device having one or more pressure sensors in accordance with an embodiment of the present invention.

A schematic diagram of device 10 is shown in FIG. 2. As shown in FIG. 2, electronic device 10 may include control circuitry such as storage and processing circuitry 40. Storage and processing circuitry 40 may include one or more different types of storage such as hard disk drive storage, nonvolatile memory (e.g., flash memory or other electrically-programmable-read-only memory), volatile memory (e.g., static or dynamic random-access-memory), etc. Processing circuitry in storage and processing circuitry 40 may be used in controlling the operation of device 10. The processing circuitry may be based on one or more microprocessors, microcontrollers, digital signal processors, baseband processor integrated circuits, application specific integrated circuits, etc.

With one suitable arrangement, storage and processing circuitry 40 may be used to run software on device 10 such as internet browsing applications, email applications, media playback applications, activity logging applications, fitness applications, operating system functions, software for capturing and processing images, software implementing functions associated with gathering and processing sensor data, software that makes adjustments to display brightness and touch sensor functionality, etc.

To support interactions with external equipment, storage and processing circuitry 40 may be used in implementing communications protocols. Communications protocols that may be implemented using storage and processing circuitry 40 include internet protocols, wireless local area network protocols (e.g., IEEE 802.11 protocols—sometimes referred to as WiFi®), protocols for other short-range wireless communications links such as the Bluetooth® protocol, etc.

Input-output circuitry 32 may be used to allow input to be supplied to device 10 from a user or external devices and to allow output to be provided from device 10 to the user or external devices.

Input-output circuitry 32 may include wired and wireless communications circuitry 34. Communications circuitry 34 may include radio-frequency (RF) transceiver circuitry formed from one or more integrated circuits, power amplifier circuitry, low-noise input amplifiers, passive RF components, one or more antennas, and other circuitry for handling RF wireless signals. Wireless signals can also be sent using light (e.g., using infrared communications). As shown in FIG. 2, circuitry 34 may include one or more radio-frequency transceivers such as cellular telephone transceiver circuitry 42 (e.g., one or more cellular telephone transmitters and/or receivers), IEEE 802.11 (WiFi®) transceiver circuitry 44 (e.g., one or more wireless local area network transmitters and/or receivers), Bluetooth® transceiver circuitry 46 such as a Bluetooth® Low Energy (Bluetooth LE) transmitter and/or receiver, and satellite navigation system receiver circuitry (e.g., a Global Positioning System receiver or other satellite navigation system receiver).

Input-output circuitry 32 may include input-output devices 36 such as buttons, joysticks, click wheels, scrolling wheels, touch screens, other components with touch sensors such as track pads or touch-sensor-based buttons, vibrators, audio components such as microphones and speakers, image capture devices such as a camera module having an image sensor and a corresponding lens system, keyboards, statusindicator lights, tone generators, key pads, keyboards and other equipment for gathering input from a user or other external source and/or generating output for a user.

Sensor circuitry such as sensors 38 of FIG. 2 may include an ambient light sensor for gathering information on ambient light levels, proximity sensor components (e.g., light-based proximity sensors and/or proximity sensors based on other structures), accelerometers, gyroscopes, magnetic sensors, and other sensor structures. Sensors 38 of FIG. 2 may, for example, include one or more microelectromechanical systems (MEMS) sensors (e.g., accelerometers, gyroscopes, microphones, force sensors, pressure sensors, capacitive sensors, or any other suitable type of sensor formed using microelectromechanical systems technology). If desired, other components in device 10 may be formed using microelectromechanical systems technology.

Device 10 may include motion characterization circuitry formed from one or more of sensors 38 and processing circuitry (e.g., storage and processing circuitry 40) that processes data from sensors 38 to determine information about how a user of device 10 is moving. In this way, processing circuitry 40 may track and characterize a user's movement and physical activity using sensors 38.

Sensors 38 may include one or more motion sensors 50 and one or more pressure sensors 62. Motion sensor 50 (sometimes referred to as motion sensor circuitry 50) may include one or more accelerometers (e.g., accelerometers that measure acceleration along one, two, or three axes), gyroscopes, compasses, pressure sensors, other suitable types of motion sensors, combinations of any two or more of these types of sensors, etc. Storage and processing circuitry in device 10 (e.g., storage and processing circuitry 40) may be used to store and process motion sensor data gathered by motion sensor 50. If desired, motion sensor circuitry 50 may be a system-on-chip integrated circuit that includes one or more motion sensors, processing circuitry, and storage (as an example).

Pressure sensor 62 (sometimes referred to as pressure sensor circuitry 62, pressure sensor structures 62, or pressure sensors 62) may include one or more pressure sensors that measure the air pressure of the surrounding environment. Pressure sensors 62 may, for example, include absolute barometric diaphragm-based pressure sensors formed from piezo-resistors embedded in a micro-machined silicon diaphragm (sometimes referred to as a piezo-resistive pressure sensor). This is, however, merely illustrative. If desired, other suitable pressure sensor technology may be used (e.g., strain gauge based pressure sensors having a metal strain gauge on a metal diaphragm, capacitive based pressure sensors having a parallel plate capacitor structure on a diaphragm, other suitable microelectromechanical systems based pressure sensors, etc.). Processing circuitry 40 may gather elevation information using pressure sensor 62. For example, processing circuitry 40 may determine the relative or absolute elevation of electronic device 10 (and thus the user holding or wearing electronic device 10) based on measured atmospheric pressure.

Processing circuitry 40 may be used to continuously or periodically track movement of device 10 using sensors such as motion sensor 50 and pressure sensor 62. In cases where device 10 is handheld, wearable, or otherwise portable, movement of device 10 may be indicative of the movement of a user of device 10. For example, when a user is holding, wearing, or otherwise carrying device 10 on his or her person, processing circuitry 40 may be used to track the user's movement based on sensor data gathered from motion sensor 50 and/or pressure sensor 62.

In some scenarios, a user may possess two or more electronic devices on his or her person. For example, a user may possess a first electronic device 10 such as a cellular telephone in his or her pocket and a second electronic device 10 such as a wrist-watch on his or her wrist. The electronic devices may be able to communicate with each other (e.g., over a wireless or wired communications path). If desired, both electronic devices may include the same set of sensors 38 or the electronic devices may include different sensors 38. In arrangements where both electronic devices include one or more sensors, sensor data from one electronic device may be used to augment the sensor data from the other electronic device, or the sensors in one electronic device may be used to calibrate the sensors in the other electronic device. In other arrangements, one electronic device may be used to process the sensor data that is gathered by sensors located in the other electronic device. For example, processing circuitry in a cellular telephone that a user is carrying may process sensor data that is gathered using sensors in a wrist-watch that the user is wearing. This is, however, merely illustrative. If desired, electronic device 10 may gather and process sensor data itself without having to rely on a second electronic device for assistance.

User movement information gathered by sensors 38 may be used in various ways. For example, applications that run on device 10 such as fitness applications, activity logging applications, mapping applications, journaling applications, and other applications may use motion sensor data from motion sensor 50 and pressure sensor data from pressure sensor 62 to track, log, and/or record a user's physical activity.

Figure 3:
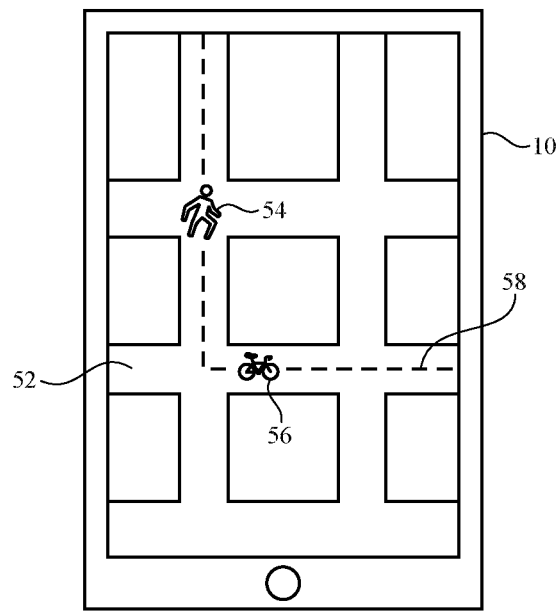
FIG. 3 is a front view of an illustrative electronic device in which motion sensor and pressure sensor data may be used to track and display a user's physical activity on a map in accordance with an embodiment of the present invention.
Figure 4:
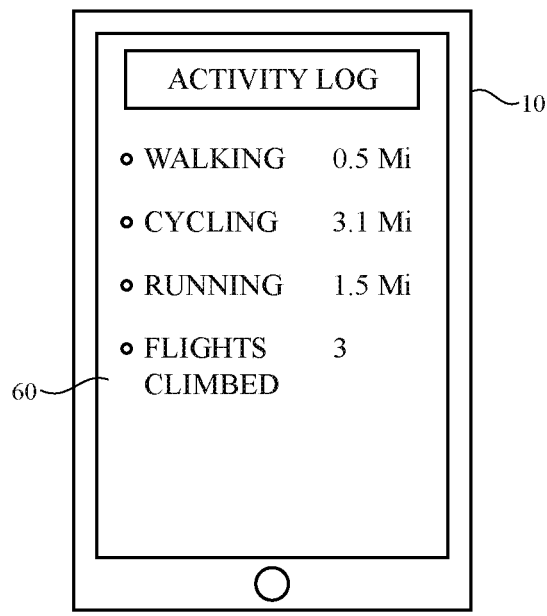
FIG. 4 is a front view of an illustrative electronic device in which motion sensor and pressure sensor data may be used to enter and display a user's physical activity in an activity log in accordance with an embodiment of the present invention.

In many of these applications, data from sensors 38 may be used not only to detect a user's movement but to determine what type of activity is being performed based on the detected motion. For example, as shown in FIG. 3, application 52 running on electronic device 10 may track and display a user's route 58 on a map. Using sensors 38, application 52 may indicate which portions of the route were walked by the user (e.g., as indicated by icon 54), which portions of the route were cycled by the user (e.g., as indicated by icon 56), which portions of the route the user climbed a flight of stairs, etc. In the example of FIG. 4, application 60 running on device 10 may display an activity log where the user can view a list physical activities performed.

The examples of FIGS. 3 and 4 are merely illustrative. In general, any suitable application may rely on sensor data from sensors 38 to track a user's motion and to determine what type of activity is being performed by the user (e.g., climbing stairs, hiking, walking, running, cycling, skiing, riding in a car, roller skating, etc.). If desired, user interface elements may be adjusted or controlled based on user activity information or applications may be launched on device 10 based on user activity information. For example, when processing circuitry 40 detects a user cycling based on data from sensors 38, a cycling application may be launched on device 10.

Processing circuitry 40 may determine which type of activity is being performed based at least partly on motion sensor data from motion sensor 50. For example, processing circuitry 40 may determine a user's cadence based on motion sensor output from motion sensor 50. Based on the user's cadence, processing circuitry 40 may determine which type of activity is being performed by the user. For example, processing circuitry 40 may determine that cadences below a given threshold correspond to walking, whereas cadences above the given threshold correspond to running (as an illustrative example).

Conventional electronic devices classify motion based solely on accelerometer output. If care is not taken, relying exclusively on accelerometer output to determine what type of activity is being performed can lead to inaccuracies. For example, accelerometer signals that are collected while a user is walking may look similar to accelerometer signals that are collected when a user is cycling. As another example, accelerometer signals that are collected when a user is cycling may look similar to accelerometer signals that are collected while a user is riding in a car experiencing low vibrations.

To avoid misclassification of a user's activity, processing circuitry 40 may use additional information to further characterize a user's movement when needed. For example, processing circuitry 40 may gather additional data such as information about a user's speed, a user's elevation, a user's geographical position, or other suitable data and may synthesize this information with motion sensor output to determine what type of activity is being performed by the user.

Different sensors may be useful in characterizing different types of activities and movements. For example, pressure sensor 62 in sensors 38 (FIG. 2) may be used to detect changes in elevation and may therefore be useful for detecting when a user is climbing stairs and for tracking the number of stairs climbed (and/or the number of flights of stairs climbed).

Changes in elevation alone may not be sufficient to determine when a user is climbing stairs. For example, pressure sensor information gathered while a user takes an escalator from a first floor in a building to a second floor of a building may look similar to pressure sensor information gathered while a user takes a set of stairs from the first floor to the second floor. To help characterize the type of movement performed by a user during an ascent or descent, processing circuitry 40 may combine pressure information from pressure sensor 62 with motion sensor information from motion sensor 50. For example, accelerometer data may be used to count a user's steps and/or to determine the user's step rate (e.g., the number of steps taken by a user over a given distance or during a given period of time). This information may be combined with pressure sensor information to determine whether stairs were climbed or whether an escalator or elevator was taken during the ascent or descent.

Figure 5:
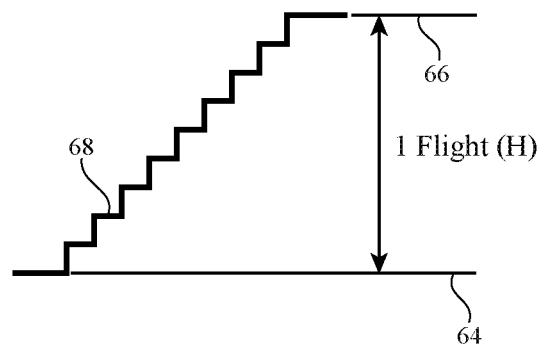
FIG. 5 is a diagram showing an illustrative flight of stairs that may be climbed by a user that is holding or wearing an electronic device with one or more pressure sensors in accordance with an embodiment of the present invention.

Some applications running on device 10 such as health monitoring or fitness tracking applications may track the number of flights of stairs climbed by the user (e.g., instead of or in addition to tracking the number of individual stairs climbed by the user). As shown in FIG. 5, for example, a single flight of stairs 68 from one floor 64 to another floor 66 may have a set number of stairs, but different individuals may use a different number of steps to climb the same number of stairs. To ensure that an individual who climbs a flight of stairs in 7 steps receives the same stair climbing credit as an individual who climbs the same flight of stairs in 9 steps, processing circuitry 40 may award flights of stairs climbed based on the vertical height climbed by the user when the stair climbing motion is detected.

After determining that the user's motion corresponds to stair climbing, processing circuitry 40 may process motion sensor and pressure sensor data to count the number of flights of stairs climbed by the user. Processing circuitry 40 may compare the vertical height climbed by the user when ascending a set of stairs to an average floor height and may award flights climbed based on this comparison. For example, if a user takes the stairs from a first floor (e.g., floor 64 of FIG. 5) to a second floor (e.g., floor 66 of FIG. 5), processing circuitry 40 may analyze pressure sensor data from pressure sensor 62 to determine the elevation change (H) and may analyze motion sensor data from motion sensor 50 to determine the number of steps taken over the elevation change (e.g., 8 steps). Based on this information, processing circuitry 40 may determine that the user is climbing stairs and that the elevation change (H) corresponds to one flight of stairs (e.g., assuming an average floor height H between consecutive floors of a building). Accordingly, processing circuitry 40 may award one flight of stairs to the user for climbing stairs 68. Health and fitness applications that run on device 10 may log (e.g., record) the single flight of stairs climbed by the user.

Figure 6:
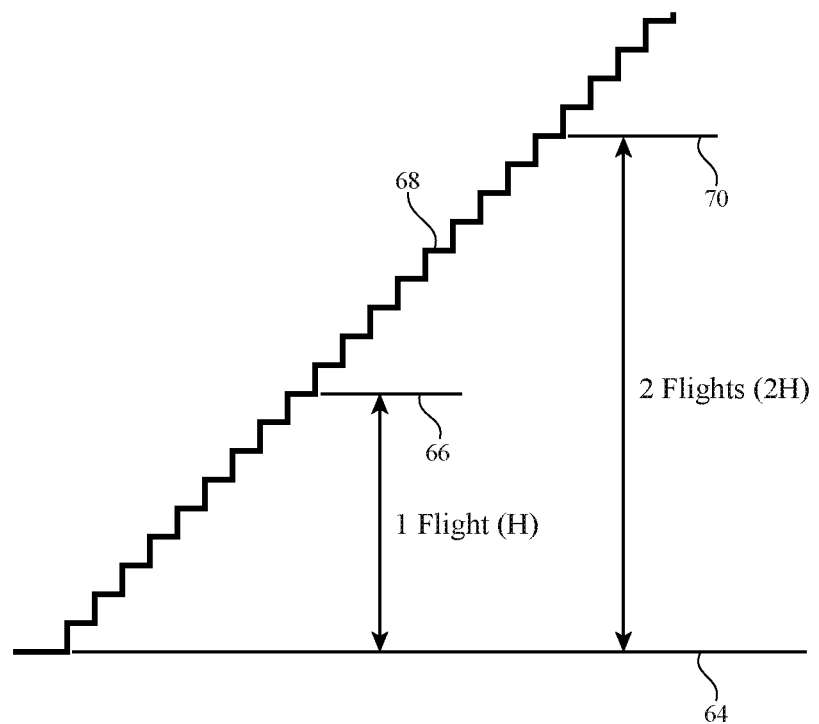
FIG. 6 is a diagram showing illustrative flights of stairs that may be climbed by a user that is holding or wearing an electronic device with one or more pressure sensors in accordance with an embodiment of the present invention.

As another example, if a user takes the stairs from a first floor (e.g., floor 64 of FIG. 6) to a third floor (e.g., floor 70 of FIG. 6) at a height 2H above the first floor, processing circuitry 40 may analyze pressure sensor data from pressure sensor 62 to determine the elevation change (2H) and may analyze motion sensor data from motion sensor 50 to determine the number of steps taken over the elevation change (e.g., 16 steps). Based on this information, processing circuitry 40 may determine that the user is climbing stairs and that the 2H elevation change corresponds to two flights of stairs (e.g., assuming an average floor height H between consecutive floors of a building). Health and fitness applications that run on device 10 may then log the two flights of stairs climbed by the user.

If desired, partial flights of stairs may be awarded to a user when the user climbs one or more flights of stairs in a building with floor heights that are not equal to the predetermined typical floor height of a building. For example, a user may be awarded 1.5 flights of stairs when the user climbs a single flight of stairs that is 1.5 times the typical floor height). This is, however, merely illustrative. In other embodiments, processing circuitry 40 may round the flights climbed to the nearest whole number of typical flights, giving at least one flight credit for every set of stairs ascended by the user. Processing circuitry 40 may keep track of the accumulated rounding error between the height of each actual flight and the height of a typical floor height, which may be used to add or subtract awarded flights when the accumulated rounding error amounts to a full flight deduction or a full flight addition.

For example, if a user takes a first set of stairs with a height amounting to 1.8 typical flights, processing circuitry 40 may give the user credit for two flights of stairs, but a debt of 0.2 flights may be stored in a "flight bank" (e.g., using storage and processing circuitry 40). If the user then takes a second set of stairs with a height amounting to 2.2 typical flights, processing circuitry 40 may subtract the 0.2 flights stored in the flight bank from the 2.2 flights so that the user is given credit for only 2 flights.

Figure 7:
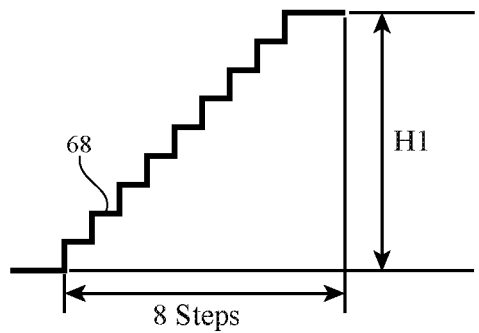
FIG. 7 is a diagram showing how steps rate may be compared with climb rate to distinguish between stair climbing and other movements in accordance with an embodiment of the present invention.
Figure 8:
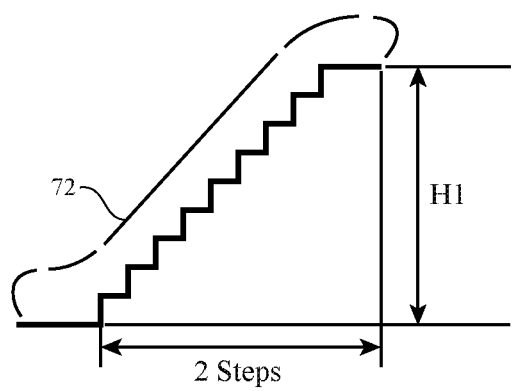
FIG. 8 is a diagram showing how step rate may be compared with climb rate to determine when a user takes an escalator in accordance with an embodiment of the present invention.
Figure 9:
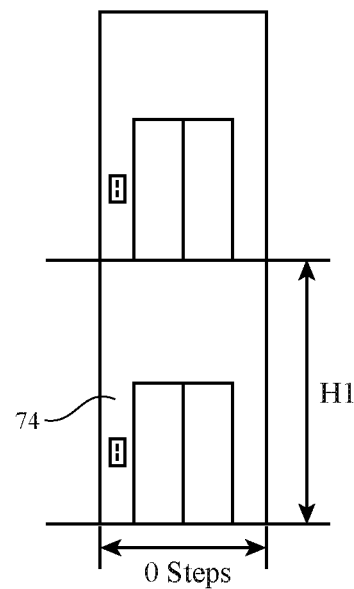
FIG. 9 is a diagram showing how step rate may be compared with climb rate to determine when a user takes an elevator in accordance with an embodiment of the present invention.

Combining cadence information from motion sensor 50 with elevation information from pressure sensor 62 may allow processing circuitry 40 to differentiate between various movements that may otherwise be confused with one another. For example, consider the example of FIG. 7 in which a user travels from the first floor of a building to the second floor of the building, where the second floor is a height H1 above the first floor (e.g., four meters or other suitable height). Processing circuitry 40 may gather pressure information from pressure sensor 62 in electronic device 10 to detect the user's four-meter-change in elevation in the period of time that the user travels from the first floor to the second floor. During the same period, processing circuitry 40 may gather motion sensor information from motion sensor 50 in electronic device 10 to determine the number of steps taken by the user during the trip from the first floor to the second floor. Based on this information, processing circuitry 40 may determine the number of steps taken by the user per change in elevation, which in turn can be used to determine whether the user is climbing stairs to the second floor or whether the user has taken some other mode of transportation to the second floor. As shown in FIG. 7, for example, eight steps over an elevation change of H1 may be indicative of stair climbing. In the example of FIG. 8, two steps over an elevation change of H1 may be indicative of riding an escalator. In FIG. 9, zero steps over an elevation change of H1 may be indicative of riding an elevator.

Thus, if processing circuitry 40 determines that eight steps are taken during the trip from the first floor to the second floor, processing circuitry 40 may give the user credit for climbing a flight of stairs (e.g., an activity logging application running on electronic device 10 may reflect that the user has climbed one flight of stairs). If processing circuitry 40 determines that two steps are taken during the trip from the first floor to the second floor, motion characterization circuitry 50 may not give the user any credit for climbing stairs (e.g., the trip to the second floor may not be logged in any application running on device 10).

If desired, processing circuitry 40 may analyze motion sensor and pressure sensor data for a predetermined period of time before an ascent and/or after an ascent to help further characterize the type of movement performed during the ascent or descent. For example, historical pressure sensor data (e.g., sensor data from 7 seconds, 5 seconds, 10 seconds, 15 or other suitable amount of time prior to detecting a user's ascent) may be used to determine whether a user was walking on level ground before beginning an ascent up a set of stairs or up a hill. If the pressure sensor indicates zero or close to zero elevation change for a period of time prior to an ascent, processing circuitry 40 may determine that a user is in a structured environment (e.g., in a building or other location where stairs are used). If the pressure sensor indicates a non-zero elevation change prior to an ascent, processing circuitry 40 may determine that a user is walking up a hill outdoors (as examples).

Differentiating between different types of ascents and descents may be useful for fitness applications or activity logging applications that log the number of stairs or flights of stairs climbed by a user. Taking the historical sensor data into account may help avoid false positives (e.g., may help avoid giving credit for stairs when in reality a user is walking uphill). This is, however, merely illustrative. If desired, processing circuitry 40 may give credit for stairs when a user walks up a steep hill (e.g., a hill that is as steep as a set of stairs).

In some arrangements, processing circuitry 40 may rely exclusively on pressure sensor data and accelerometer data to determine whether and at what rate a user is climbing stairs. In other arrangements, processing circuitry 40 may supplement the pressure sensor data and accelerometer data with additional information to further reduce the risk of false positives. For example, information from other sensors 38 in device 10, information about applications running on device 10, and/or information based on user input may provide additional insight as to whether a user is climbing a flight of stairs. For example, if a cycling application that logs a user's trip while cycling is running on device 10, processing circuitry 40 may determine that the user is not climbing stairs even if the changes in elevation and/or steps per second are similar to those detected when a user is climbing stairs.

If desired, processing circuitry 40 may use the pressure sensor 62 to determine a user's relative change in elevation and a user's absolute elevation. An estimate of a user's absolute elevation may be useful in converting pressure changes detected by a pressure sensor into relative elevation changes. For example, a one meter change in elevation at sea level may result in a pressure change of about 12 Pa, whereas a one meter change in elevation at a mile above sea level may result in a pressure change of about 10 Pa. Processing circuitry 40 may, if desired, adjust the algorithm used to convert pressure sensor data into changes in elevation based on the user's estimated elevation above sea level.

Figure 10:
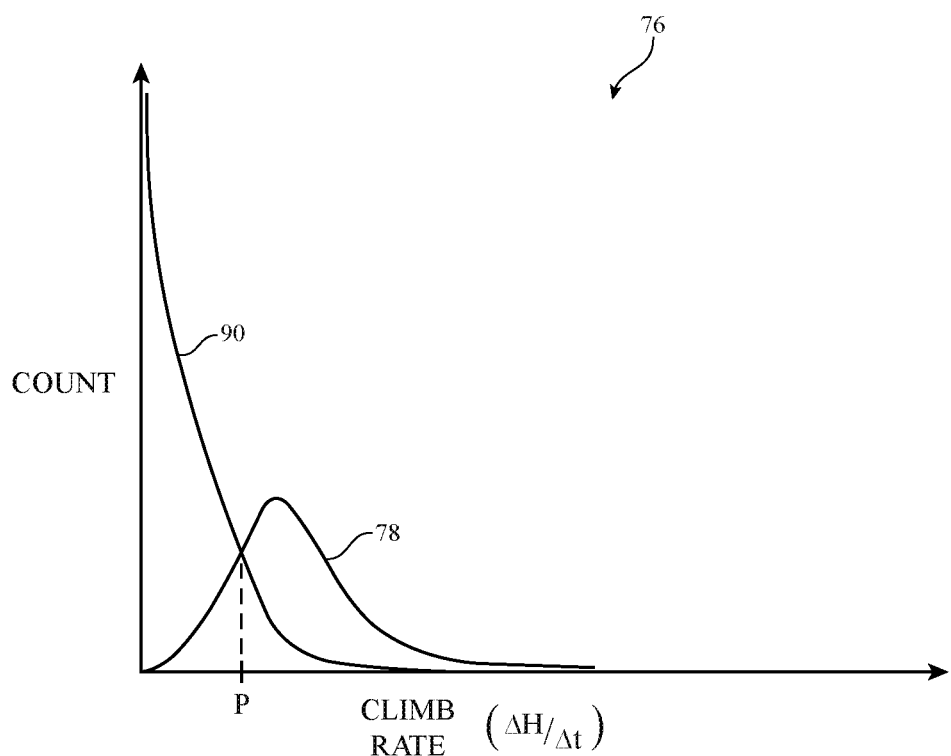
FIG. 10 is a histogram showing an illustrative distribution of climb rate data showing how a minimum climb rate may be used to identify when a user begins to climb a flight of stairs in accordance with an embodiment of the present invention.

During operation of device 10, processing circuitry 40 may monitor pressure data and motion data until a minimum climb rate is detected. Once a minimum climb rate is detected, processing circuitry 40 may begin counting flights of stairs. FIG. 10 illustrates how using a minimum climb rate can be used to detect stair climbing. Graph 76 of FIG. 10 is a histogram showing an illustrative distribution of climb rate data gathered using pressure sensor 62. Curve 90 illustrates the distribution of data gathered while a user walks on flat ground (with minor elevation changes), and curve 78 illustrates the distribution of data gathered while a user walks up a set of stairs. The climb rate may correspond to the user's change in elevation over a given sample period (e.g., 5 seconds, 10 seconds, 15 seconds, less than 5 seconds, more than five sections, etc.)

Value P of FIG. 10 represents a minimum climb rate that processing circuitry 40 may use to determine when a user is climbing a set of stairs. When processing circuitry 40 detects a climb rate below value P, processing circuitry 40 may determine that the user is not ascending stairs. When processing circuitry 40 detects a climb rate at or above value P, processing circuitry 40 may determine that the user is ascending stairs and may initiate a flight counting algorithm. If desired, processing circuitry 40 may process historical motion data and pressure data corresponding to a period of time prior to detecting the minimum climb rate to incorporate this data into the flight counting algorithm, or processing circuitry 40 may ignore the historical data and may initiate flight counting from the time the minimum climb rate is detected.

Figure 11:
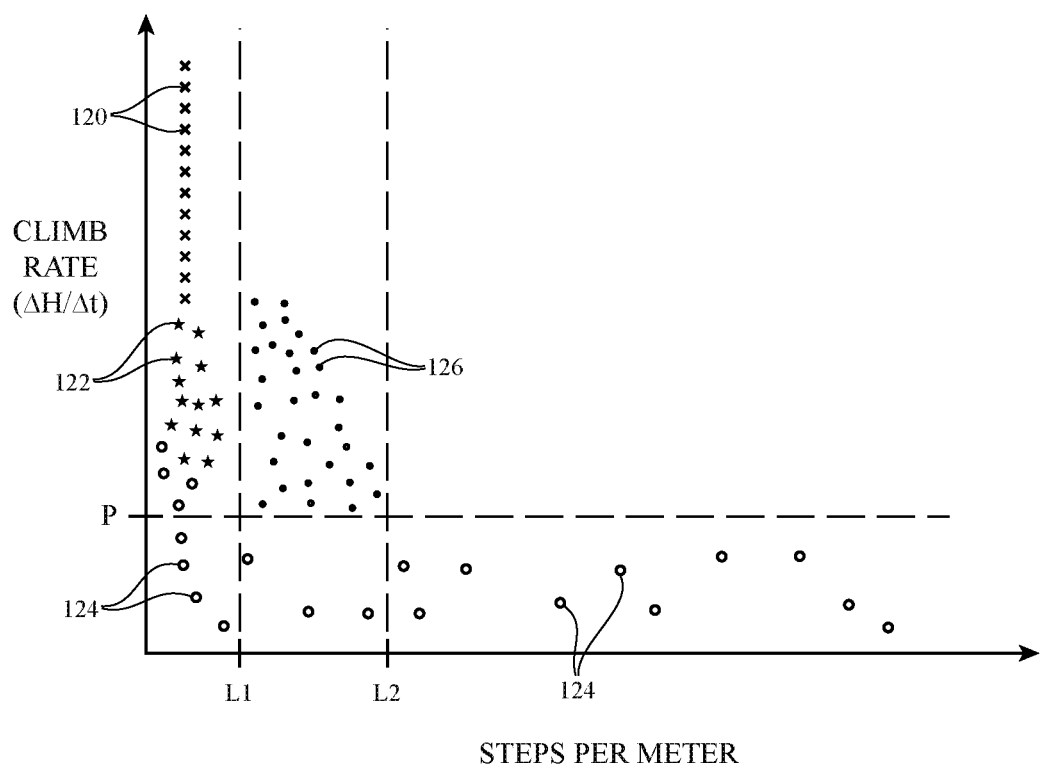
FIG. 11 is a graph of illustrative data showing how climb rate and step rate may be used to differentiate one type of movement from another type of movement.

FIG. 11 is a graph illustrating how additional thresholds may be used to distinguish between stair climbing and other activities. FIG. 11 shows illustrative data for various movements. Data points 120 illustrate climb rate and step rate for users riding elevators; data points 122 illustrate climb rate and step rate for users riding escalators; data points 124 illustrate climb rate and step rate for users walking on flat ground (e.g., flat ground with minor elevation changes); and data points 126 illustrate climb rate and step rate for users climbing stairs.

As shown in FIG. 11, minimum climb rate P may be used to distinguish travel on flat ground (points 124) from upward travel such as travel from one floor to another floor in a building (points 120, 124, and 126). Step rate limits L1 and L2 may be used to distinguish stair climbing (points 126) from other modes of travel between floors. Step rates below L1 may correspond to non-stair-climbing movements such as riding an elevator (points 120) and riding an escalator (points 122). Upper step rate limit L2 from may be imposed to distinguish stair climbing from other upward movements that may result in high step rate measurements (e.g., cycling, riding in a car on a bumpy road, etc.).

Figure 12:
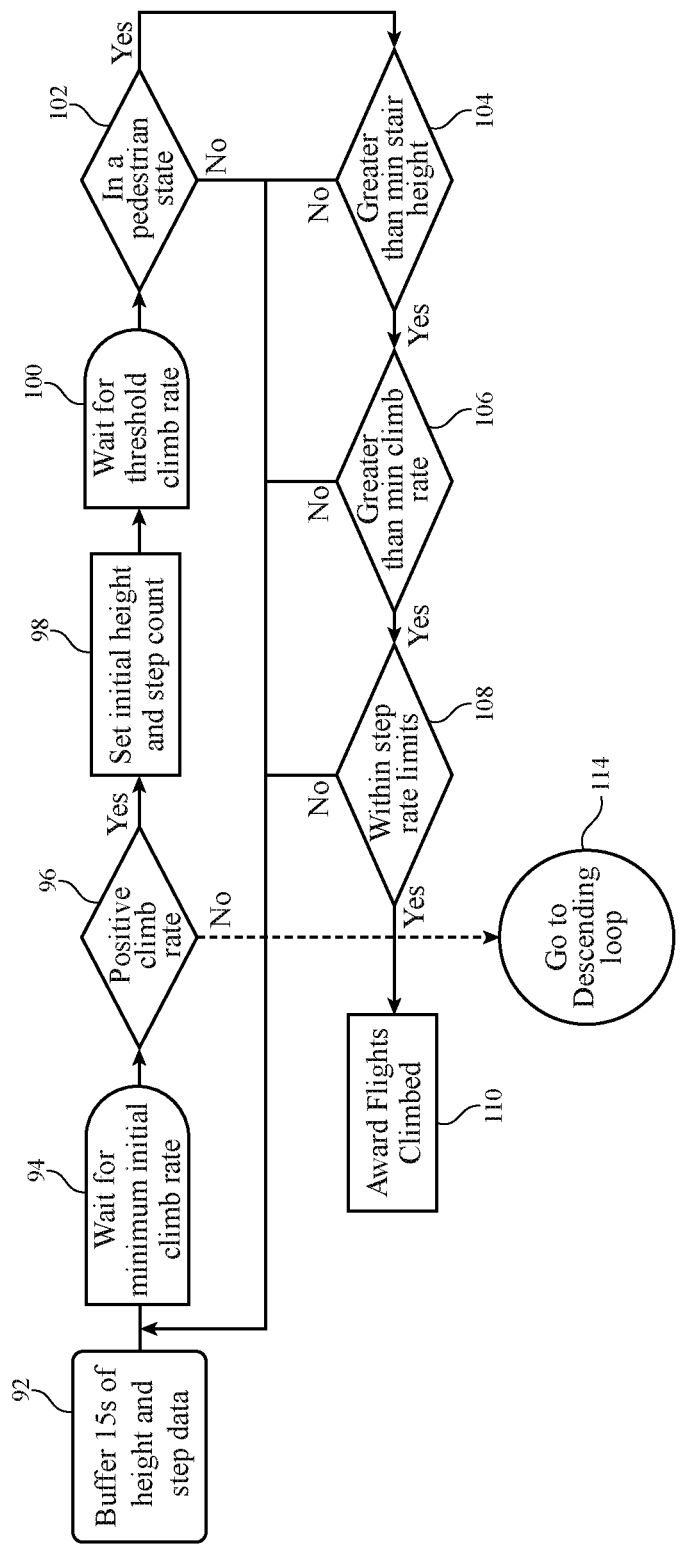
FIG. 12 is a flow chart of illustrative steps involved in counting the number of flights of stairs climbed by a user using motion sensor and pressure sensor data in accordance with an embodiment of the present invention.

FIG. 12 is a flow chart of illustrative steps involved in operating an electronic device with flight counting capabilities (e.g., electronic device 10 of FIG. 1). At step 92, storage and processing circuitry 40 may store a predetermined number of samples of step data from motion sensor 50 and elevation data from pressure sensor 62 in a buffer for processing. The processing may include, for example, aligning the step data samples with the elevation data samples to remove any time lag between the step data samples and elevation data samples. The buffered data may correspond to a period of 15 seconds, 10 seconds, 30 seconds, 20 seconds, or other suitable amount of time.

Processing circuitry 40 may analyze elevation data to determine a climb rate (e.g., a user's change in elevation over a given period of time). During step 94, processing circuitry 40 may continue calculating a user's climb rate until the climb rate matches or exceeds a predetermined minimum initial climb rate (e.g., climb rate P of FIGS. 10 and 11). When the user's climb rate exceeds the minimum initial climb rate, processing circuitry 40 may determine whether the climb rate is positive (step 96). If the climb rate is negative, processing may proceed to a descending loop in which the sensor data is processed using a different algorithm. For example, the descending loop may include tracking the number of flights descended or may include monitoring sensor data until a different movement or activity is detected. If it is determined in step 96 that the climb rate is positive, processing may proceed to step 98.

At step 98, processing circuitry 40 may set the initial height and step count to a given set of values based on the gathered step data and elevation data. The initial height and step count correspond to the elevation and step count at the beginning of the user's ascent. At step 100, processing circuitry 40 may continue calculating a user's climb rate until the climb rate falls below a predetermined threshold climb rate. When the user's climb rate falls below the threshold climb rate (e.g., when the user has reached the top of a set of stairs and begins to walk on flat ground), processing circuitry 40 may process the sensor data gathered during the user's ascent. This may include, at step 102, determining whether the user is in a pedestrian state (102). Motion sensor data from sensor 50 and/or other sensor data from other sensors may be used to determine if the user is in a pedestrian state (i.e., on foot). If the user is not in a pedestrian state (e.g., if the user is on a bicycle or in a car), processing may loop back to step 94.

If, on the other hand, the user is in a pedestrian state, processing may proceed to step 104. At step 104, processing circuitry 40 may determine whether the total change in elevation during the user's ascent is greater than a minimum stair height. If the change in elevation is less than the minimum stair height, processing may loop back to step 94. If the total change in elevation is greater than a minimum stair height, processing may proceed to step 106.

At step 106, processing circuitry 40 may determine whether the user's climb rate (e.g., the average climb rate) during the ascent is greater than a predetermined minimum climb rate (e.g., point P of FIG. 11 or other suitable threshold value). If the climb rate is less than the minimum climb rate, processing may loop back to step 94. If the climb rate is greater than the minimum climb rate, processing may proceed to step 108. At step 108, processing circuitry 40 may determine whether the user's step rate during the ascent is within upper and lower step rate limits (e.g., L1 and L2 of FIG. 11). If the step rate is not within the step limits, processing may loop back to step 94. If the step rate is within the step rate limits, processing may proceed to step 110. At step 110, processing circuitry 40 may credit flights climbed to the user based on the change in elevation over the period of ascent.

Figure 13:
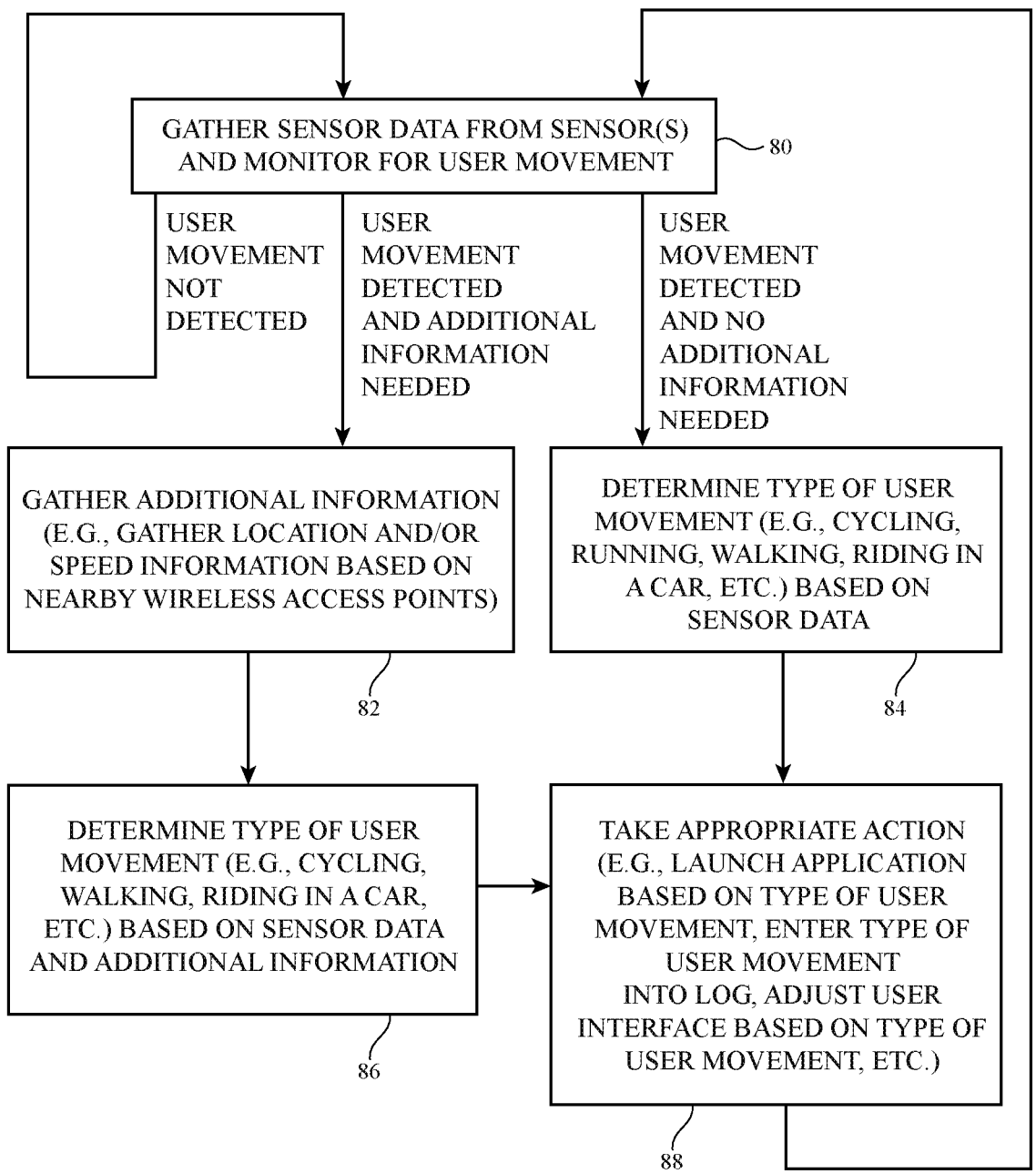
FIG. 13 is a flow chart of illustrative steps involved in tracking and characterizing a user's physical activity using an electronic device in accordance with an embodiment of the present invention.

FIG. 13 is a flow chart of illustrative steps involved in tracking and characterizing a user's physical activity using an electronic device such as electronic device 10 of FIG. 1.

At step 80, processing circuitry 40 may gather sensor data from one or more motion sensors 50 (e.g., from one or more accelerometers, gyroscopes, compasses, pressure sensors, etc.) and may monitor for user movement. In configurations where motion sensor circuitry is set to continuously track a user's activity (e.g., for a fitness application running on device 10 or other suitable application), step 80 may be repeated until the user's movement is detected. If desired, processing circuitry 40 may gather additional sensor data such as pressure sensor data from pressure sensor 62 during step 80.

In some instances, motion sensor output may be unambiguously indicative of a particular type of activity. For example, motion sensor signals collected while a user is running may be uniquely associated with running. As another example, motion sensor signals collected while a user is cycling at 100 RPM may be uniquely associated with cycling. When motion sensor signals are indicative of only one particular type of activity, processing may proceed to step 84.

At step 84, processing circuitry 40 may determine what type of activity is being performed by the user (e.g., running, cycling, walking, riding in a car, etc.) based on the gathered motion sensor data.

In instances where motion sensor data gathered in step 80 is not uniquely associated with a particular type of user activity (e.g., where motion sensor signals are associated with more than one type of activity), processing may proceed from step 80 to step 82.

At step 82, processing circuitry 40 may gather additional information such as information about the user's elevation, location, and/or speed to assist in accurately identifying the type of activity associated with the gathered motion sensor data. For example, a user's change in elevation may be determined based on pressure information gathered using pressure sensor 62 in electronic device 10. As another example, wireless transceiver circuitry 44 may be used to take one or more snapshots of local wireless access points within a vicinity of electronic device 10. This information may be used to determine the approximate location of device 10 and how the user's location changes over time. In locations where local wireless access points are few and far between (e.g., in rural areas), processing circuitry 40 may gather location information from other sources such as Global Positioning System receiver circuitry 48.

By supplementing motion sensor data with additional information (e.g., location information) only when motion sensor data alone is insufficient for classifying motion, power savings may be achieved. Additional power savings may be achieved by relying on Global Positioning System receiver circuitry to obtain location information only when local wireless access points are not available.

At step 86, processing circuitry 40 may associate the gathered motion sensor data with a single type of activity using the additional information gathered in step 82 (e.g., based on the number of steps taken by the user for a given change in elevation, based on the user's average speed as determined through WiFi®-assisted positioning, etc.). For example, for a given cadence detected by the motion sensor, speeds over a given threshold may correspond to one activity (e.g., cycling) while speeds under the given threshold may correspond to a different activity (e.g., walking).

At step 88, device 10 may take appropriate action. For example, processing circuitry 40 may launch an application on device 10 based on the type of activity detected (e.g., a cycling application may be launched upon detection of a user cycling), the user's activity may be recorded or entered into an activity journaling application, user interface elements bay be adjusted or controlled based on the type of activity detected, etc. Processing may then optionally loop back to step 80 to continue tracking and/or monitoring for user activity.

The foregoing is merely illustrative of the principles of this invention and various modifications can be made by those skilled in the art without departing from the scope and spirit of the invention.

What is claimed is:

1. A portable electronic device, comprising:
   a motion sensor that gathers motion sensor data indicative of a step rate of a user;
   a pressure sensor that gathers pressure information indicative of a rate of elevation change of the user; and
   processing circuitry that characterizes the user's movement based on the motion sensor data and the pressure information, wherein the processing circuitry determines that the user is climbing stairs when the step rate exceeds a threshold step rate and the rate of elevation change exceeds a threshold rate of the elevation change.

2. The portable electronic device defined in claim 1 wherein the processing circuitry determines that the user is cycling when the step rate exceeds an additional threshold step rate that is greater than the threshold step rate and when the rate of elevation change exceeds the threshold rate of elevation change.

3. The portable electronic device defined in claim 2 wherein the processing circuitry determines that the user is climbing stairs when the step rate is below the additional threshold step rate.

4. The portable electronic device defined in claim 1 wherein the motion sensor comprises an accelerometer.

5. The portable electronic device defined in claim 4 wherein the processing circuitry tracks the user's steps using the accelerometer.

6. The portable electronic device defined in claim 5 wherein the processing circuitry tracks changes in the user's elevation using the pressure sensor.

7. The portable electronic device defined in claim 6 wherein the processing circuitry determines a number of flights of stairs climbed by the user based on the user's steps and the changes in the user's elevation.

8. The portable electronic device defined in claim 7 further comprising a display that displays the number of flights of stairs climbed by the user.

9. A method for operating an electronic device having a motion sensor, a pressure sensor, and processing circuitry, the method comprising:
   with the motion sensor, gathering motion sensor data indicative of a step rate of a user;
   with the pressure sensor, gathering pressure information indicative of a rate of elevation change of the user; and
   with the processing circuitry, determining that the user is climbing stairs when the step rate exceeds a threshold step rate and the rate of elevation change exceeds a threshold rate of elevation change.

10. The method defined in claim 9 further comprising determining whether the user is performing an activity based on the step rate and the rate of elevation change, wherein the activity is selected from the group consisting of: walking, cycling, and running.

11. The method defined in claim 10 wherein determining that the user is climbing stairs comprises:
    with the processing circuitry, determining a number of steps taken by the user in a given period of time; and
    with the processing circuitry, determining the user's change in elevation in the given period of time.

12. The method defined in claim 11 wherein determining that the user is climbing stairs comprises determining that the step rate is below an additional threshold step rate that is greater than the threshold step rate.

13. The method defined in claim 12 further comprising determining that the user is cycling when the step rate exceeds the additional threshold step rate.

14. The method defined in claim 12 further comprising:
    in response to determining that the user is climbing stairs, determining a number of flights of stairs climbed by the user.

15. The method defined in claim 14 wherein determining the number of flights of stairs climbed by the user comprises comparing the user's change in elevation with a predetermined average floor height.

16. A method for operating an electronic device having a pressure sensor, a motion sensor, and processing circuitry, comprising:
    with the motion sensor, gathering data indicative of a user's step rate;
    with the pressure sensor, gathering data indicative of the user's rate of elevation change; and
    determining whether the user is climbing stairs by determining whether the user's step rate is between first and second threshold step rates and based on whether the user's rate of elevation change exceeds a threshold rate of elevation change.

17. The method defined in claim 16 further comprising determining that the user is cycling when the user's step rate exceeds the first and second threshold step rates and the user's rate of elevation change exceeds the threshold rate of elevation change.

18. The method defined in claim 16 further comprising:
    in response to determining that the user is climbing stairs, tracking and storing a number of flights of stairs climbed by the user.

19. The method defined in claim 18 wherein tracking the number of flights of stairs climbed by the user comprises:
    tracking changes in elevation with the pressure sensor; and
    comparing the changes in elevation with a predetermined floor height.

20. The method defined in claim 16 further comprising:
    when the user's step rate is below the first and second threshold step rates and the user's rate of elevation change exceeds the threshold rate of elevation change, determining that the user is performing an activity selected from the group consisting of: riding an escalator and riding an elevator.

* * * * *